(12) United States Patent
Loose et al.

(10) Patent No.: US 9,062,682 B2
(45) Date of Patent: Jun. 23, 2015

(54) APPLICATIONS OF PUMP PERFORMANCE MONITORING

(75) Inventors: Douglas H. Loose, Southington, CT (US); Christian Victor O'Keefe, Durham, CT (US); Robert J. Maron, Middletown, CT (US); Joseph L. Poplawski, Wallingford, CT (US); Michael A. Davis, Glastonbury, CT (US); Mark R. Fernald, Enfield, CT (US); Timothy J. Bailey, Longmeadow, MA (US)

(73) Assignee: CiDRA CORPORATE SERVICES INC.

( * ) Notice: Subject to any disclaimer, the term of this patent is extended or adjusted under 35 U.S.C. 154(b) by 910 days.

(21) Appl. No.: 12/992,927
(22) PCT Filed: May 20, 2009
(86) PCT No.: PCT/US2009/044658
§ 371 (c)(1),
(2), (4) Date: Feb. 1, 2011
(87) PCT Pub. No.: WO2009/143232
PCT Pub. Date: Nov. 26, 2009

(65) Prior Publication Data
US 2011/0118998 A1    May 19, 2011

Related U.S. Application Data
(60) Provisional application No. 61/054,901, filed on May 21, 2008, provisional application No. 61/054,732, (Continued)

(51) Int. Cl.
*G06F 19/00* (2011.01)
*G01N 29/14* (2006.01)
(Continued)

(52) U.S. Cl.
CPC .............. *F04D 15/0088* (2013.01); *G01H 1/00* (2013.01); *G01N 29/14* (2013.01)

(58) Field of Classification Search
CPC .... G06F 19/00; G01N 29/14; G01N 30/8665; E21B 47/0007
USPC ................. 702/54, 33–36, 39, 41, 45, 47–48, 702/50–52, 56, 81, 84, 98, 100, 103, 105, 702/127, 138, 140, 142–143, 145, 182–183, 702/185, 189; 73/1.16, 1.19, 1.35, 1.37, 73/1.57, 1.68, 1.82–1.84, 40, 40.5 A, 73/170.11, 170.13–170.14, 278–279, 455, 73/570, 587, 592–593, 645–646, 660, 700, 73/702–703, 715, 861, 861.18, 861.42, 73/861.47; 415/89, 97, 99, 120; 417/19–20, 22, 44.2–44.3, 44.8–44.9
See application file for complete search history.

(56) References Cited

U.S. PATENT DOCUMENTS

| 5,249,932 A | 10/1993 | Van Bork |
| 5,575,310 A | 11/1996 | Kamen et al. |

(Continued)

FOREIGN PATENT DOCUMENTS

| FR | 2974633 | 11/2012 |
| WO | 9208957 | 5/1992 |

OTHER PUBLICATIONS

Choi et al., Experiments on the Unsteady Flow Field and Noise Generation in a Centrifugal Pump Impeller, 2003, Journal of Sound and Vibration 263, pp. 493-514.*
(Continued)

*Primary Examiner* — Toan Le

(57) ABSTRACT

The present invention provides a processor or signal processing module that features one or more modules configured to receive an input signal containing information about the unsteady pressures or acoustic emissions caused by a medium flowing through a pump, and also configured to provide of an output signal containing information about the performance of the pump. The information about the performance of the pump may include information about pump performance monitoring by a slip flow measurement, about predicting impeller wear, about pump impeller cavitation monitoring, about pump monitoring through acoustic emissions, about pump leak detection, about pump efficiency monitoring and about positive displacement pump monitoring.

45 Claims, 6 Drawing Sheets

Related U.S. Application Data filed on May 20, 2008, provisional application No. 61/054,608, filed on May 20, 2008, provisional application No. 61/054,600, filed on May 20, 2008, provisional application No. 61/054,592, filed on May 20, 2008, provisional application No. 61/054,575, filed on May 20, 2008, provisional application No. 61/054,566, filed on May 20, 2008.

(51) Int. Cl.
  *F04D 15/00* (2006.01)
  *G01H 1/00* (2006.01)

(56) References Cited

U.S. PATENT DOCUMENTS

| | | |
|---|---|---|
| 7,134,320 B2 | 11/2006 | Gysling et al. |
| 7,165,464 B2 | 1/2007 | Gysling et al. |
| 7,343,820 B2 | 3/2008 | Gysling et al. |
| 7,363,800 B2 | 4/2008 | Gysling |
| 7,367,240 B2 | 5/2008 | Gysling et al. |
| 2001/0015107 A1 | 8/2001 | Feller |
| 2004/0030524 A1* | 2/2004 | Jarrell et al. ............ 702/113 |
| 2004/0141420 A1* | 7/2004 | Hardage et al. ............ 367/149 |
| 2005/0011278 A1 | 1/2005 | Brown et al. |
| 2006/0071666 A1 | 4/2006 | Unsworth et al. |
| 2007/0006727 A1 | 1/2007 | Gysling |
| 2007/0044572 A1 | 3/2007 | Davis et al. |

OTHER PUBLICATIONS

J.F. Gulich, Selection Criteria for Suction Impellers of Centrifugal Pumps, Mar. 2001, World Pumps, pp. 22-27.*

Rus et al., An Investigation of the Relationship Between Acoustic Emission, Vibration, Noise, and Cavitation Structures on a Kaplan Turbine, Sep. 2007, Transactions of the ASME, vol. 129, pp. 1112-1122.*

International Search Report dated Jul. 14, 2009 issued in Intl. Patent Application No. PCT/US2009/044658 (3 pages).

FR2974633 English language abstract (1 page), Nov. 2, 2012.

* cited by examiner

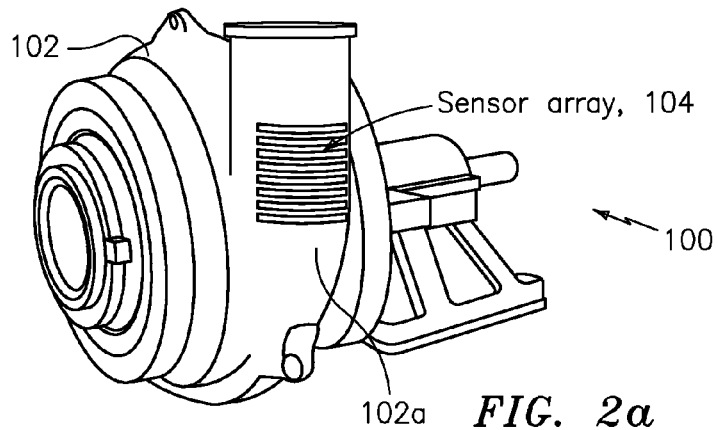
FIG. 2a
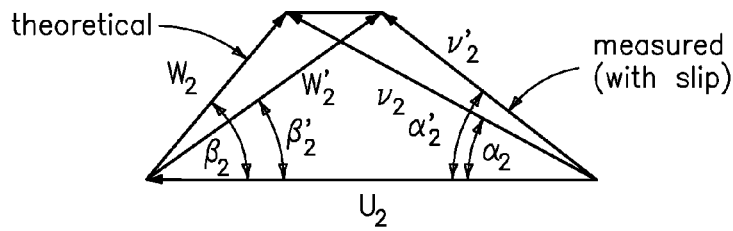
FIG. 2b
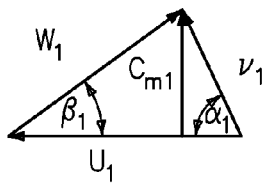
Inlet velocities at $R_1$
FIG. 2c(i)
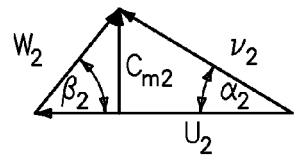
Outlet velocities at $R_2$
FIG. 2c(ii)
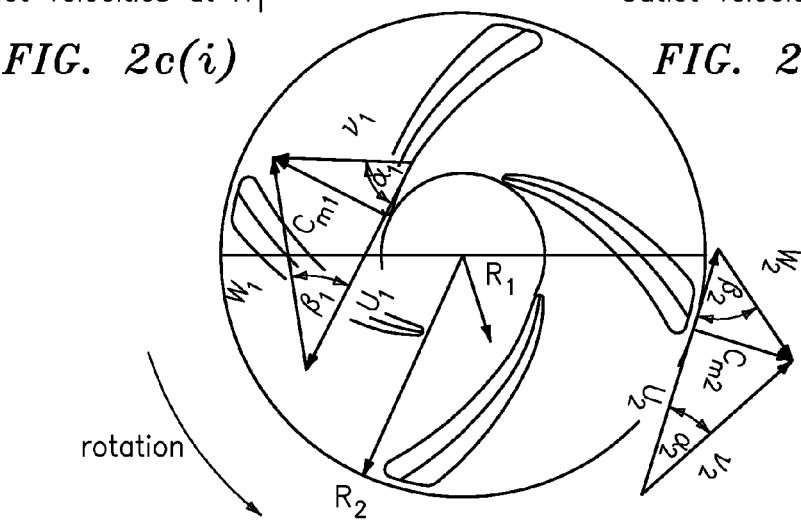
FIG. 2c(iii)

Pump Startup

Pump Cavitation

APPLICATIONS OF PUMP PERFORMANCE MONITORING

CROSS-REFERENCE TO RELATED APPLICATIONS

This application corresponds to international patent application serial no. PCT/US2009/044658, filed 20 May 2009, which claims benefit to provisional patent application Ser. No. 61/054,566; Ser. No. 61/054,575; Ser. No. 61/054,592; Ser. No. 61/054,600; Ser. No. 61/054,608; and Ser. No. 61/054,732; all filed May 20, 2008, as well as Ser. No. 61/054,901, filed May 21, 2008, which are all incorporated by reference in their entirety.

BACKGROUND OF THE INVENTION

1. Field of Invention

This invention relates to techniques for monitoring the performance of a pump; and more particularly, this invention relates to techniques for monitoring the performance of a pump based at least partly on unsteady pressures or acoustic emissions sensed in relation to the pump using, e.g., SONAR-based and/or PVDF-based sensor technology.

2. Description of Related Art

Techniques are known for monitoring the performance of pumps, including the monitoring of various components of the pump, as well as monitoring the efficiency of the pump. The pumps may include among others centrifugal, bladder, piston or positive displacement pumps. The following is a brief description of some known pump conditions or parameters that are important to pump performance, known techniques for monitoring pump performance as well as some of drawbacks related to the known techniques:

For example, the slip of a centrifugal pump is an important parameter in determining the efficiency of the pump. The greater the slip the lower the effective efficiency. Wear in an impeller and/or a casing or liner of a pump can increase the slip and thereby reduce efficiency of the pump.

In addition, centrifugal pumps are used extensively throughout industry, in applications ranging from processing clean liquids through heavy slurries. A typical problem that these pumps can exhibit is cavitation near the impeller of the pump. The cavitation of small bubbles on the surface of the vanes of an impeller will erode and pit the impeller. This will result in degraded performance of the pump and if the conditions causing the cavitation are not rectified will likely cause impeller failure.

Moreover, it is known in the art that many aspects of the health of a pump can be obtained by taking accelerometer measurements in various locations on, or in relation to, a pump. Details of internal bearing health can be determined by the vibration readings obtained from the accelerometers and any excessive vibration can indicate damage to internal components. However, often these measurements provide information only after damage has occurred. Typically, wear components of a pump will likely induce vibrations in the pump and will also likely produce acoustic emissions. Existing systems are available that will monitor the airborne acoustics around a pump; however, these systems have to filter out the emissions from only the pump of interest. In addition, by the time the acoustic emissions become airborne they often have been attenuated greatly and are difficult to measure.

Further, leaks around bearings and mating surfaces can be a problem in high pressure applications if not quickly identified and fixed. Typically, a small high pressure leak will have an associated high frequency acoustic emission. This acoustic frequency will be higher than the vibration and other acoustic frequencies present on a typical pump.

Furthermore, one type of pump typically used for high viscosity or pressure applications are positive displacements pumps. These pumps operate by forcing fluid from an inlet pressure section of the pump into the discharge section. Several variations of these pumps exist, although most employ a valve or sealing mechanism to isolate the inlet from the discharge during the pressurization phase of the pump.

Finally, the overall efficiency of an electric-motor driven pump may be defined as the power delivered to the fluid (the water horsepower) divided by the electric power delivered to the motor:

$$\eta = \frac{Q \times (P_{DISCHARFGE} - P_{INTAJKE})}{W},$$

where:
Q=flow rate, m3/sec,
$P_{DISCHARGE}$=Pump discharge pressure, Pa,
$P_{INTAKE}$=Pump intake pressure, Pa, and
W=Electrical power, Watts.

The pump/motor efficiency will be less than one due to system losses which can include fluid leakage (through impeller clearances), friction, mechanical (bearings, seals, etc.) in the pump and the electric motor efficiency.

The operator of a pump will generally want to run the pump at the highest possible efficiency for a given set of flow conditions. However, over time as the pump is used the efficiency will decrease either 1) gradually due to normal wear or 2) suddenly due to mechanical failure or damage. In either case, there will be an optimum point at which maintenance action to restore lost efficiency would be beneficial. The operator's dilemma is deciding when to perform maintenance, because maintenance done too soon or too late can significantly impact overall cost to the operator.

The pump efficiency as defined above can be calculated by measuring the flow rate through the pump, the intake and discharge pressures (or the DP between the intake and the discharge) and the power to the electric motor.

In view of the aforementioned, there is a need in the industry for new techniques for the monitoring of the performance of pumps, including among others centrifugal, bladder, piston or positive displacement pumps.

SUMMARY OF THE INVENTION

The Signal Processor Module

In its broadest sense, the present invention provides new and unique techniques for monitoring pump performance that may be used in one or more of the aforementioned applications.

According to some embodiments of the present invention, apparatus for implementing the techniques may take the form of a processor or signal processing module that features one or more modules configured to receive an input signal containing information about the unsteady pressures and/or acoustic emissions caused by a medium flowing through a pump, and also configured to provide of an output signal containing information about the performance of the pump.

The information about the performance of the pump may include information about (1) pump performance monitoring by a slip flow measurement, (2) monitoring related to predicting impeller wear, (3) pump impeller cavitation monitoring, (4) pump monitoring through acoustic emissions, (5) monitoring related to pump leak detection, (6) pump efficiency monitoring and (7) positive displacement pump monitoring.

The processor or signal processing module may be used in relation to one or more pump systems featuring a pump and one or more PVDF-based and/or SONAR-based sensors for monitoring the performance of the pump, based at least partly on unsteady pressures and/or acoustic emissions sensed on, or in relation to, the pump, consistent with that described below:

The Basic Pump System

Some embodiments of the present invention may take the form of a pump system featuring a pump; one or more sensors, including PVDF-based and/or SONAR-based sensors, arranged on, or in relation to, the pump, configured to respond to unsteady pressures and/or acoustic emissions caused by a medium flowing through the pump, and to provide a signal containing information about the same; and a signal processing module configured to receive the signal containing information about the unsteady pressures and/or acoustic emissions caused by the medium flowing through the pump, and also configured to provide of an output signal containing information about the performance of the pump.

Pump Performance Monitoring by Slip Flow Measurement

Some embodiments of the present invention may take the form of a pump system featuring a pump having a casing or a liner; a SONAR-based array of sensors arranged on the casing or liner, and configured to respond to unsteady pressures caused by a medium flowing through the pump, including the unsteady pressures caused by an impeller tip velocity and a fluid velocity, and to provide a signal containing information about the same; and a signal processing module that may be configured to receive the signal containing information about the unsteady pressures caused by the medium flowing through the pump, and may also be configured to provide of an output signal containing information about a slip flow measurement that can be related to the pump performance.

According to some embodiments of the present invention, the signal processing module may be configured to determine the velocity of an impeller tip and the fluid velocity of the medium in real time based at least partly on pressure measurements that are a function of the spacing between sensors in a SONAR-based array and the transition time between the sensors.

Pump Performance Monitoring Using SONAR-Based Technology

Some embodiments of the present invention may take the form of a pump system featuring a pump having an impeller, a casing, a suction inlet or a discharge; a SONAR-based array of sensors arranged on the casing, suction inlet or discharge, and configured to respond to unsteady pressures caused by a medium flowing through the pump, and to provide a signal containing information about the same; and a signal processing module that may be configured to receive the signal containing information about the unsteady pressures caused by the medium flowing through the pump, and also may be configured to provide of an output signal containing information about wear of parts of the pump, including wear in the back shroud or eye of the impeller.

Pump Impeller Cavitation Monitoring

Some embodiments of the present invention may take the form of a pump system featuring a pump, such as a centrifugal pump, having a pump body and an impeller, and being coupled to inlet and outlet piping; one or more piezofilm or strip sensors (also known as PVDF) arranged in relation to the pump body or inlet and outlet piping, and configured to respond to acoustic emissions caused by a medium flowing through the pump, including the collapsing of small bubbles caused by the cavitation process created within the pump, and to provide a signal containing information about the same; and a signal processing module that may be configured to receive the signal containing information about the acoustic emissions caused by the medium flowing through the pump, and also may be configured to provide of an output signal containing information about pump impeller cavitation monitoring, including wear of the impeller caused by the cavitation process.

According to some embodiments of the present invention, the signal processing module may be configured to compare characteristic frequencies of the acoustic emissions of the pump at startup to associated characteristic frequencies of the acoustic emissions of the pump at a later time caused by the cavitation process.

Pump Monitoring Through Acoustic Emissions

Some embodiments of the present invention may take the form of a pump system featuring a pump having an inlet and outlet; one or more PVDF-based sensors attached to either the inlet, or the outlet or both of the pump, and configured to respond to acoustic emissions caused by a medium flowing through the pump, including the collapsing of small bubbles caused by the cavitation process created within the pump, and to provide a signal containing information about the same; and a signal processing module that may be configured to receive the signal containing information about the acoustic emissions caused by the medium flowing through the pump, and also may be configured to provide of an output signal containing information about pump monitoring through acoustic emissions, including information about cavitation, bearing wear, impeller wear or casing liner damage.

According to some embodiments of the present invention, the signal processing module may be configured to measure and track signature characteristic pump frequencies over time and determine pump wear or potential failure based on variations in frequency or amplitude in the signature characteristic pump frequencies.

According to some embodiments of the present invention, the acoustic emissions may be monitored while they travel in the fluid on either the inlet or outlet of the pump. The PVDF-based sensors may be attached to either the inside or the outside of a pipe can be used to monitor the acoustic emissions from the pump and can be used to detect conditions such as the cavitation, bearing wear, impeller wear and casing liner damage.

Monitoring for Pump Leak Detection

Some embodiments of the present invention may take the form of a pump system featuring a pump, including bladder or piston pumps; a SONAR-based array of sensors attached to one or more parts or surfaces of the pump, including an inlet of the pump, and configured to respond to unsteady pressures caused by a medium flowing through the pump, including leaks in internal valves and around bearings and mating surfaces leaks, and to provide a signal containing information about the same; and a signal processing module that may be configured to receive the signal containing information about the unsteady pressures caused by the medium flowing through the pump, and may also be configured to provide of an output signal containing information about pump leak detection, including information about the leaks in internal valves and around bearings and mating surfaces.

According to some embodiment of the present invention, the signal processing module may be configured to check the coherence of a frequency signal and determine an emission direction that can be used for the pump leak detection.

According to some embodiment of the present invention, the acoustic measurement abilities of the SONAR-based array can be used to identify a specific high frequency. In addition, the array processing capabilities of the system can be used to check the coherence of the frequency signal and determine an emission direction.

Pump Efficiency Monitoring

Some embodiments of the present invention may take the form of a pump system featuring a pump; a SONAR-based array of sensors attached to one or more parts or surfaces of the pump, including an inlet of the pump, and configured to respond to unsteady pressures caused by a medium flowing through the pump, and to provide a signal containing information about the same; and a signal processing module that may be configured to receive the signal containing information about the unsteady pressures caused by the medium flowing through the pump, and may also be configured to provide of an output signal containing information about pump efficiency monitoring leak detection, based at least partly on the rate of flow of the medium through the pump.

According to some embodiment of the present invention, the signal processing module may be configured to provide the output signal based at least partly in responds to signalling containing information about intake and discharge pressure and electrical power measurements.

According to some embodiment of the present invention, a technique is provided to monitor the performance of a pump using a SONAR-based flow meter to measure the flow rate of the pumped medium. The SONAR-based flow meter, can be used to measure the flow rate through the pump. The SONAR-based technique of flow rate measurement is especially beneficial for liquid slurry flows or particle-laden gas flows where, due to the erosive characteristics of the flow, any intrusive method of flow measurement would be subject to excessive wear and premature failure. The present invention of using the SONAR-based flow meter may be used in combination with pressure and electrical power measurements that enables pump efficiency to be monitored continuously and in real-time.

Positive Displacement Pump Monitoring

Some embodiments of the present invention may take the form of a pump system featuring a positive displacement pump; a SONAR-based array of sensors attached to one or more parts or surfaces of the pump, and configured to respond to unsteady pressures and acoustic emissions caused by a medium flowing through the pump, and to provide a signal containing information about the same; and a signal processing module that may be configured to receive the signal containing information about the unsteady pressures and acoustic emissions caused by the medium flowing through the pump, and may also be configured to provide of an output signal containing information about positive displacement pump monitoring, based at least partly on the rate of flow of the pump versus the number of pumping strokes.

According to some embodiments of the present invention, the information about the rate of flow of the pump may be based at least partly on the unsteady pressures, and the number of pumping strokes is based at least partly on the acoustic emissions.

The Method

According to some embodiments, the present invention may also take the form of a method comprising steps for receiving an input signal containing information about the unsteady pressures or acoustic emissions caused by a medium flowing through a pump; and providing of an output signal containing information about the performance of the pump. This method may also comprise other steps for implementing the functionality set forth herein.

Computer-Readable Storage Medium

According to some embodiments of the present invention, the apparatus may also take the form of a computer-readable storage medium having computer-executable components for performing the steps of the aforementioned method.

BRIEF DESCRIPTION OF THE DRAWING

The drawing includes FIGS. 1-7b, which are not drawn to scale, as follows:

FIG. 2a is a block diagram of a pump system having pump performance monitoring by a slip flow measurement according to some embodiments of the present invention.

FIG. 2b is a diagram showing measured velocity (with slip) and theoretical velocity related to the pump system in FIG. 2a.

FIGS. 2c(i), 2c(ii) and 2c(iii) are diagrams respectively showing inlet velocity, outlet velocity, and an ideal velocity profile in an impeller for the pump system in FIG. 2a.

FIG. 4b is a graph of frequency versus time showing characteristic frequencies present at a pump startup related to the pump system in FIG. 4a.

FIG. 4c is a graph of frequency versus time showing characteristic frequencies present at a pump cavitation related to the pump system in FIG. 4a.

FIG. 6b is a graph of a pump signature of acoustic emissions related to the pump system shown in FIG. 6a.

DETAILED DESCRIPTION OF BEST MODE OF THE INVENTION

FIG. 1a

The Signal Processor Module

Figure 1A:
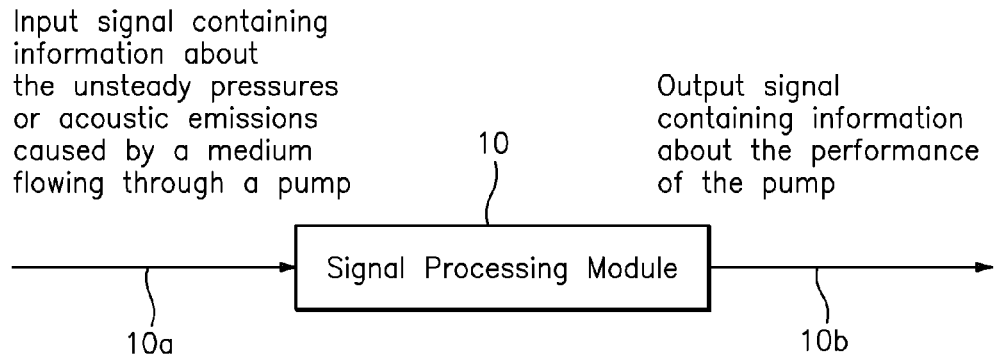
FIG. 1a is a block diagram of a signal processing module according to some embodiments of the present invention.

FIG. 1a shows a processor or signal processing module generally indicated as 10 that features one or more modules configured to receive an input signal along line 10a containing information about the unsteady pressures and/or acoustic emissions caused by a medium flowing through a pump, and also configured to provide of an output signal along line 10b containing information about the performance of the pump.

The information about the performance of the pump may include information about (1) pump performance monitoring by a slip flow measurement, (2) monitoring related to predicting impeller wear, (3) pump impeller cavitation monitoring, (4) pump monitoring through acoustic emissions, (5) monitoring related to pump leak detection, (6) pump efficiency monitoring and (7) positive displacement pump monitoring, consistent with that shown and described herein.

The functionality of the processor or signal processing module 10 may be implemented using hardware, software, firmware, or a combination thereof. In a typical software implementation, the processor modules would include one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology either now known or later developed in the future.

The processor or signal processing module 10 may be used in relation to one or more pump systems featuring a pump, including centrifugal, bladder, piston or positive displacement pumps, and sensors, including PVDF-based or SONAR-based sensors, for monitoring the performance of the pump, based at least partly on unsteady pressures and/or acoustic emissions sensed on, or in relation to, the pump, consistent with that described below:

FIG. 1b

The Basic Pump System

Some embodiments of the present invention may take the form of a pump system generally indicated 20 featuring a pump 22; one or more sensors 24, including PVDF-based and/or SONAR-based sensors, arranged on, or in relation to, the pump 22, configured to respond to unsteady pressures and/or acoustic emissions caused by a medium flowing through the pump 22, and to provide a signal containing information about the same; and the signal processing module 10 (see FIG. 1a) configured to receive the signal containing information about the unsteady pressures and/or acoustic emissions caused by the medium flowing through the pump, and also configured to provide of the output signal containing information about the performance of the pump.

The scope of the invention is intended to include pumps like centrifugal, bladder, piston or positive displacement pumps that are known in the art, as well as other types or kinds of pumps either now known or later developed in the future.

Moreover, the scope of the invention is intended to include sensors like PVDF-based sensors for sensing acoustic emissions or SONAR-based sensors for sensing unsteady pressures that are known in the art, as well as other types or kinds of sensors for sensing the same either now known or later developed in the future. By way of example, the sensors 24 may take the form in whole or in part of sensors disclosed in U.S. Pat. Nos. 7,165,464; 7,134,320; 7,363,800; 7,367,240; and 7,343,820, all of which are incorporated by reference in their entirety. By way of example, the sensors disclosed in the aforementioned patents may be configured to sense the volumetric flow of the medium and provide a signal containing information about the volumetric flow that is not substantially affected by the varying amounts of entrained air in the medium. As a person skilled in the art would appreciate, PVDF-based sensors are made from Polyvinylidene Fluoride, which is a highly non-reactive and pure thermoplastic fluoropolymer. The scope of the invention is also intended to include other types or kinds of SONAR-based VF/GVF meters either now known or later developed in the future that perform the same basic functionality of the SONAR-based VF/GVF meter as such functionality relates to implementing the present invention.

FIGS. 2a-2c(iii)

Pump Performance Monitor by Slip Flow Measurement

Figure 1B:
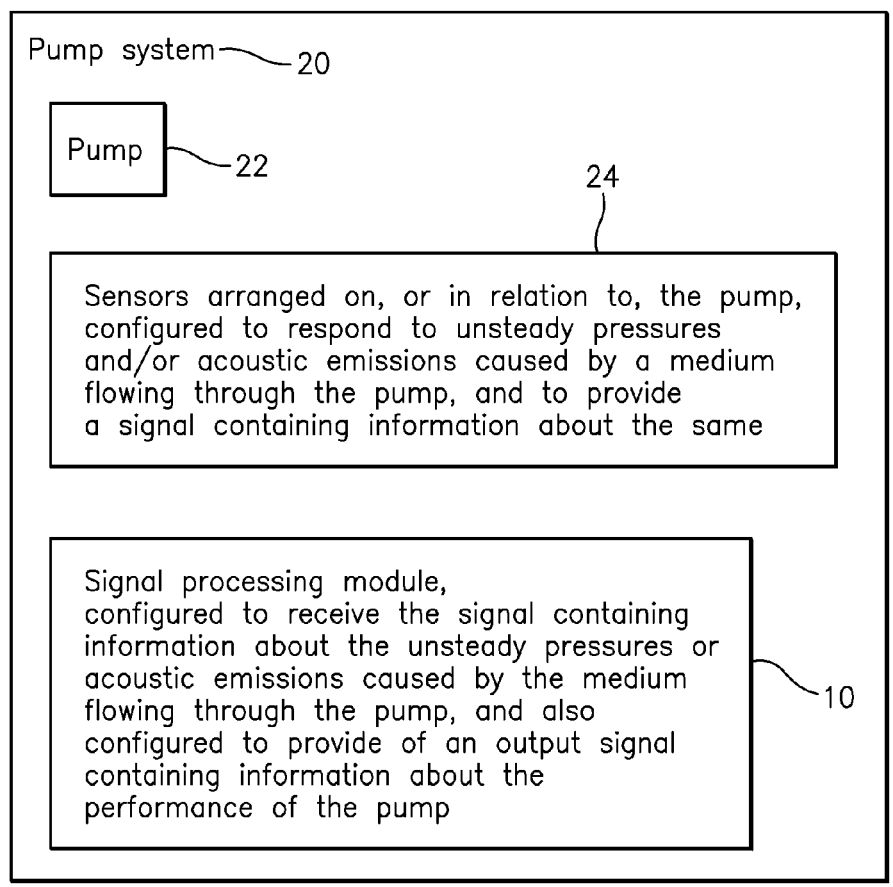
FIG. 1b is a block diagram of a pump system according to some embodiments of the present invention.

FIG. 2a shows a pump system generally indicated as 100 featuring a pump 102 and a SONAR-based array of sensors 104, as well as the signal processing module, such as module 10 (FIGS. 1a, 1b) according to some embodiments of the present invention.

The pump has a casing or liner 102a.

The SONAR-based array 104 of sensors is arranged on the casing or liner 102a, and configured to respond to unsteady pressures caused by a medium flowing through the pump 102, including the unsteady pressures caused by an impeller tip velocity and a fluid velocity, and to provide a signal containing information about the same.

The signal processing module, such as module 10 (FIG. 1a), may be configured to receive the signal containing information about the unsteady pressures caused by the medium flowing through the pump, and may also be configured to provide of an output signal containing information about a slip flow measurement.

According to some embodiments of the present invention, the signal processing module, such as module 10 (FIGS. 1a, 1b), and the SONAR-based sensor array 104 may be configured to measure slip and ideal velocities. This velocity is the actual impeller tip velocity. The fluid itself will typically have a reduced velocity due to the slip. The sensor array 104 may be installed on the casing, as shown, in the proper location to measure the unsteady pressures created by both the impeller tip velocity and the fluid velocity in real time. From these pressure measurements, the signal processing module, such as module 10 (FIG. 1a), can be configured to determine the velocities of each knowing the spacing between sensors in the array 104 and the transition time between sensors. As wear occurs on the impeller, the slip will increase and the difference between the ideal and slip velocity can be monitored and the severity of wear can be determined on a real time basis.

This invention proposes using an array sensors to measure the slip and ideal velocities. FIGS. 2b, 2c(ii) and 2c(iii) show the ideal velocity denoted as V2. This velocity is the actual impeller tip velocity. The fluid itself will have a reduced velocity due to the slip. This is denoted as V2' in FIG. 2b.

The pump system 100 or pump 102 may also include one or more elements, devices, apparatus or equipment that are known in the art, do not form part of the underlying invention, and are not disclosed herein or described in detail for that reason.

The scope of the invention re the pump applications is not intended to be limited to the type or kind of medium being processed, or the type of pumping process, either now known or later developed in the future.

Figure 3A:
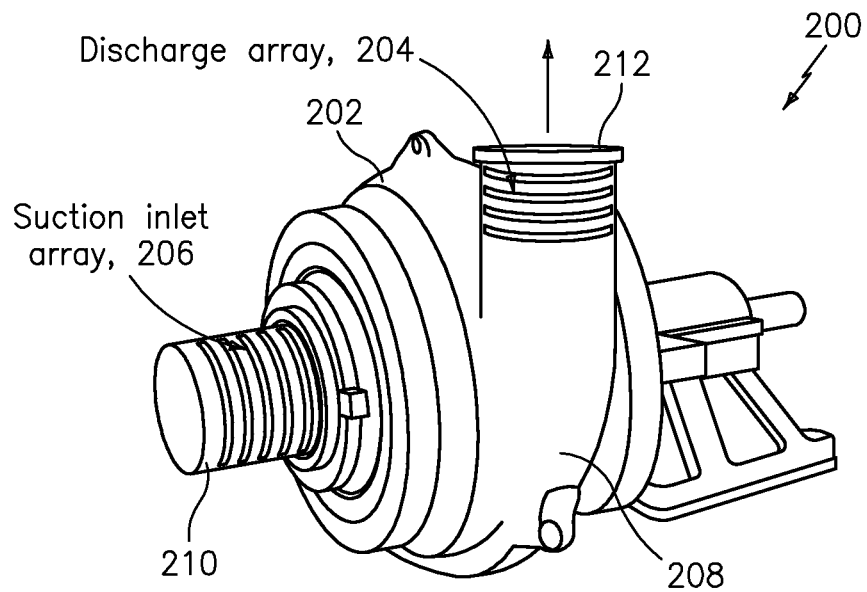
FIG. 3a is a block diagram of a pump system having pump performance monitoring using integrated SONAR-based technology according to some embodiments of the present invention.
Figure 3B:
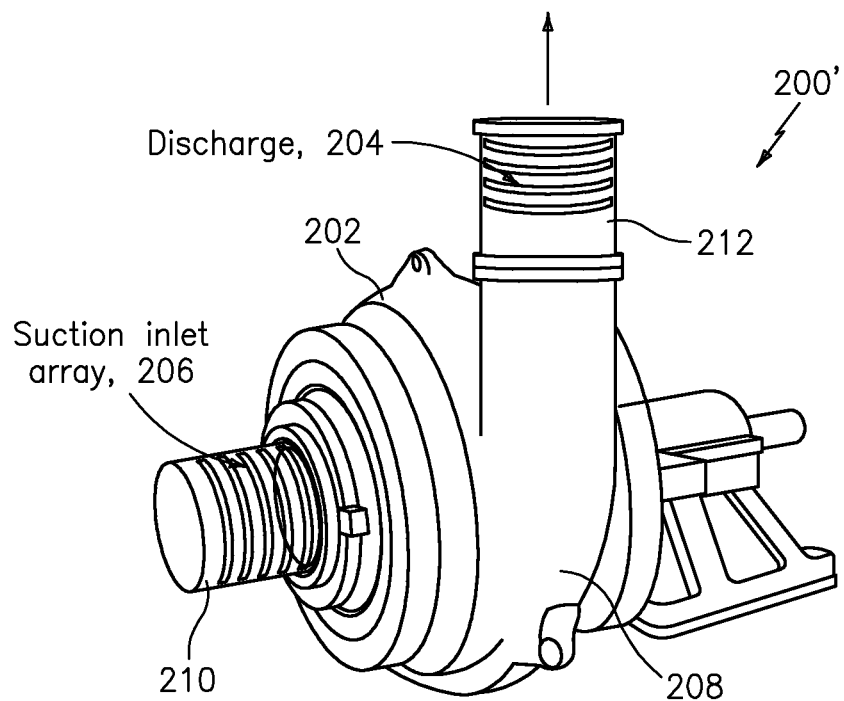
FIG. 3b is a block diagram of a pump system having pump performance monitoring using external SONAR-based technology according to some embodiments of the present invention.

FIGS. 3a, 3b

Pump Performance Monitoring Using SONAR-Based Technology

FIGS. 3a and 3b show a pump system generally indicated as 200, 200' featuring a pump 202 and a SONAR-based array 204, 206 of sensors, along with the signal processing module, such as module 10 (FIGS. 1a, 1b), according to some embodiments of the present invention. Similar parts in FIGS. 3a, 3b are identified using similar reference numerals.

The pump 202 has an impeller (see FIG. 4a), a casing 208, a suction inlet 210 or a discharge 212.

The SONAR-based array(s) 204, 206 of sensors is arranged on the casing 208, suction inlet 210 or discharge 212, and may be configured to respond to unsteady pressures caused by a medium flowing through the pump 202, and to provide a signal containing information about the same. The SONAR array(s) 210, 212 can be integrated as shown in FIG. 3a or externally fixtured to pump 202 as shown in FIG. 3b.

The signal processing module 10 (FIGS. 1a, 1b) may be configured to receive the signal containing information about the unsteady pressures caused by the medium flowing through the pump 202, and also may be configured to provide of an output signal containing information about the wear of parts of the pump 202, including wear in the back shroud or eye of the impeller.

As a person skilled in the art would appreciate, the velocity within the discharge 212 and suction end 210 of pumps can be a good indicator for determining the performance of a pump and predicting wear. The signal processing module 10 (FIGS. 1a, 1b) and SONAR-based meter may be configured to measure the unsteady pressures and determine the convection velocity. Integrating this technology within the pump casing 208, discharge 212 and or inlet 210, the velocity of the flow can be determined from which the performance of the pump can be obtained. For example, as a person skilled in the art would appreciate, when high velocities are present within the impeller accelerated wear will likely occur on the back shroud of the impeller. Alternatively, if low velocities are present excessive wear due to recirculation of the slurry back to the eye of the impeller will likely cause the eye to wear.

The pump system 200 or pump 202 may also include one or more elements, devices, apparatus or equipment that are known in the art, do not form part of the underlying invention, and are not disclosed herein or described in detail for that reason.

Figure 4A:
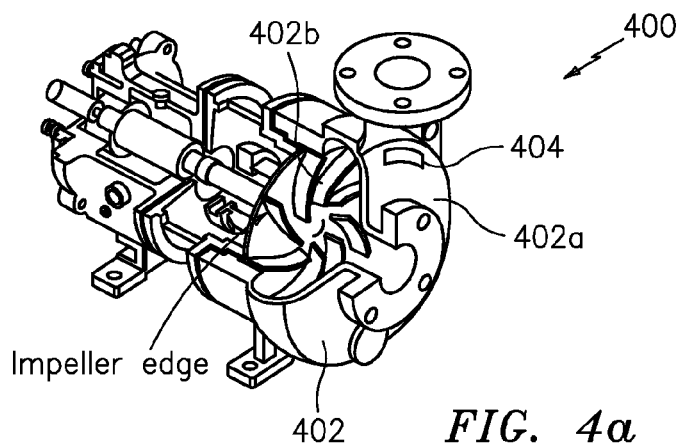
FIG. 4a is a block diagram of a pump system having pump performance monitoring using pump impeller cavitation monitoring according to some embodiments of the present invention.
Figure 4B:
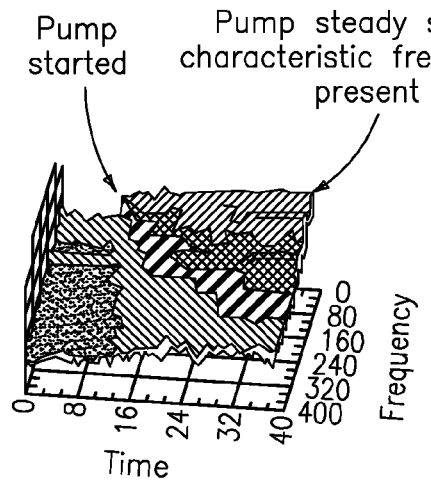
Figure 4C:
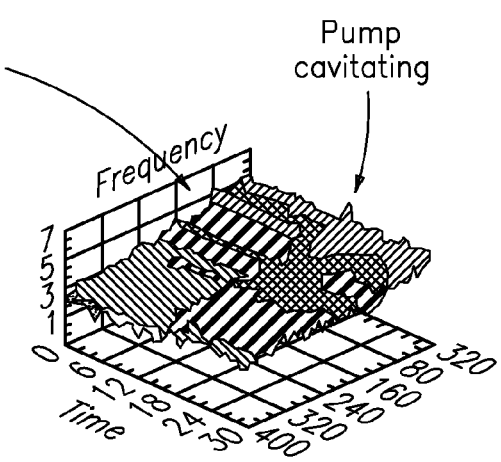

FIGS. 4a-4c

Pump Impeller Cavitation Monitoring

FIG. 4a shows a pump system generally indicated as 400 featuring a centrifugal pump 402 and one or more PVDF-based sensors 404, along with the signal processing module, such as module 10 (FIGS. 1a, 1b), according to some embodiments of the present invention.

Figure 7A:
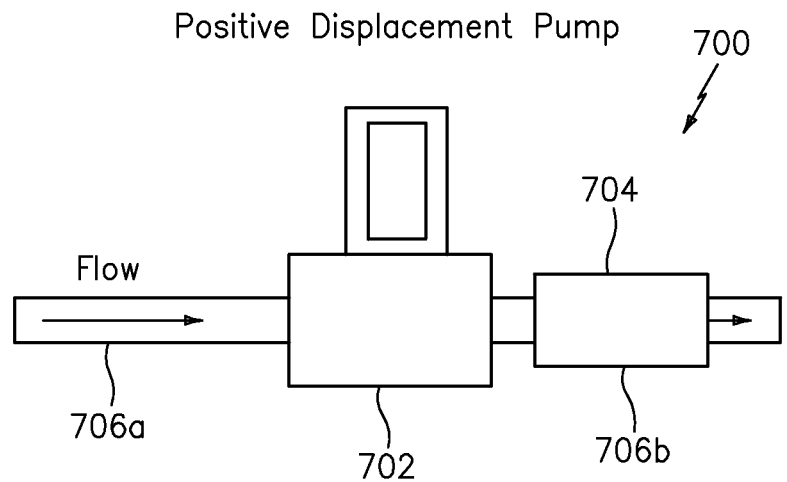
FIG. 7a is a block diagram of a positive displacement pump system being monitored, e.g., by measuring the flow produced by the pump versus the number of pumping strokes, according to some embodiments of the present invention.

The centrifugal pump 402 has a pump body and an impeller 402b, and may be coupled to inlet and outlet piping (see, e.g., inlet and outlet piping elements 706a, 706b in FIG. 7a).

The one or more PVDF-based sensors 404 may be arranged in relation to the pump body 402a, as well as the inlet and outlet piping, and is configured to respond to acoustic emissions caused by a medium flowing through the pump 402, including the collapsing of small bubbles caused by the cavitation process created within the pump 402, and to provide a signal containing information about the same.

The signal processing module 10 (FIGS. 1a, 1b) may be configured to receive the signal containing information about the acoustic emissions caused by the medium flowing through the pump, and may also be configured to provide of an output signal containing information about pump impeller cavitation monitoring, including wear of the impeller caused by the cavitation process.

According to some embodiments of the present invention, the signal processing module 10 (FIGS. 1a, 1b) may be configured to compare characteristic frequencies of the acoustic emissions of the pump 402 at startup to associated characteristic frequencies of the acoustic emissions of the pump 402 at a later time caused by the cavitation process.

As a person skilled in the art would appreciate, during the cavitation process, the collapsing of the small bubbles that are created can create acoustic emissions within the pump 402. These acoustic emissions can be detected by the one or more PVDF-based sensors 404 and used to identify when cavitation is occurring within the pump. Since the inlet and outlet piping to the pump can act as waveguides to the acoustics generated within the pump the one or more PVDF-based sensors 404 can be located in multiple locations; on the pump body itself 402a or along the piping (not shown) attached to the pump.

FIG. 4b shows the detection of pump cavitation through the use of the PVDF-based sensors 404 attached to the inlet side of the centrifugal pump 402. As seen in the chart in FIG. 4b, a pump is started and quickly reaches steady state operation. The chart in FIG. 4c demonstrates the acoustic emissions caused by cavitation occurring within the pump. Changes were made to the line pressure causing the pump to begin to cavitate, as indicated by the changes about half way through the data in the chart in FIG. 4c. A dramatic change in the acoustic emissions are observed across a wide range of acoustic frequencies.

The pump system 400 or pump 402 may also include one or more elements, devices, apparatus or equipment that are known in the art, do not form part of the underlying invention, and are not disclosed herein or described in detail for that reason.

FIG. 5

Pump Monitoring Through Acoustic Emissions

Figure 5:
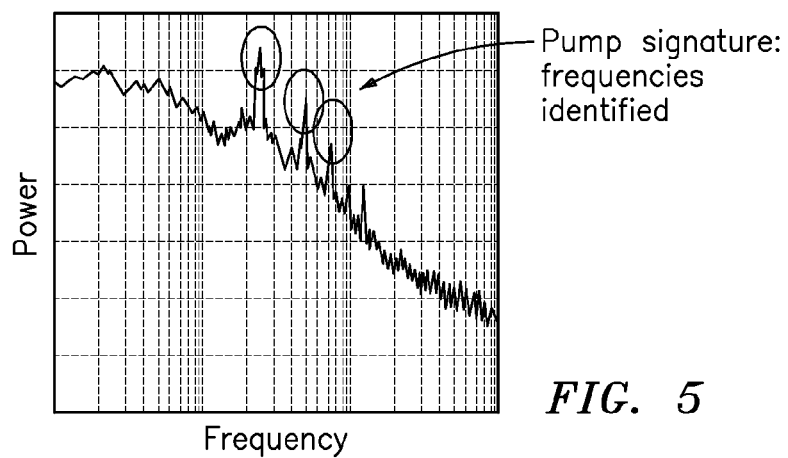
FIG. 5 is a graph of a pump signature taken with PVDF-based sensors related to a pump system being monitored through acoustic emissions.

There are many equipment diagnostic data analysis techniques that can be utilized to monitor and detect when a pump is malfunctioning, according to the present invention described herein. One such method utilizes a pump "signature" which is taken during normal steady-state operation of the pump. From this type of pump signature characteristic, pump frequencies can be measured and tracked over time. Variations in the frequencies present or the amplitudes of the signals can indicate pump wear and potential failure. FIG. 5 shows an example of a pump signature taken with PVDF-based sensors.

According to some embodiments of the present invention, the acoustic emissions may be monitored while they travel in the fluid on either the inlet or outlet of the pump. The PVDF-based sensors may be attached to either the inside or the outside of a pipe can be used to monitor the acoustic emissions from the pump and can be used to detect conditions such as the cavitation, bearing wear, impeller wear and casing liner damage.

Some embodiments of the present invention using this type of technique may take the form of a pump system featuring a pump having an inlet and outlet; one or more PVDF-based sensors attached to either the inlet, or the outlet or both of the pump, and configured to respond to acoustic emissions caused by a medium flowing through the pump, including the collapsing of small bubbles caused by the cavitation process created within the pump, and to provide a signal containing information about the same; and a signal processing module that may be configured to receive the signal containing information about the acoustic emissions caused by the medium flowing through the pump, and also may be configured to provide of an output signal containing information about pump monitoring through acoustic emissions, including information about the cavitation, bearing wear, impeller wear or casing liner damage.

According to some embodiments of the present invention, the signal processing module such as 10 (FIGS. 1a, 1b) may be configured to measure and track signature characteristic pump frequencies over time and determine pump wear or potential failure based on variations in frequency or amplitude in the signature characteristic pump frequencies.

FIG. 6a, 6b

Pump Leak Detection

Figure 6A:
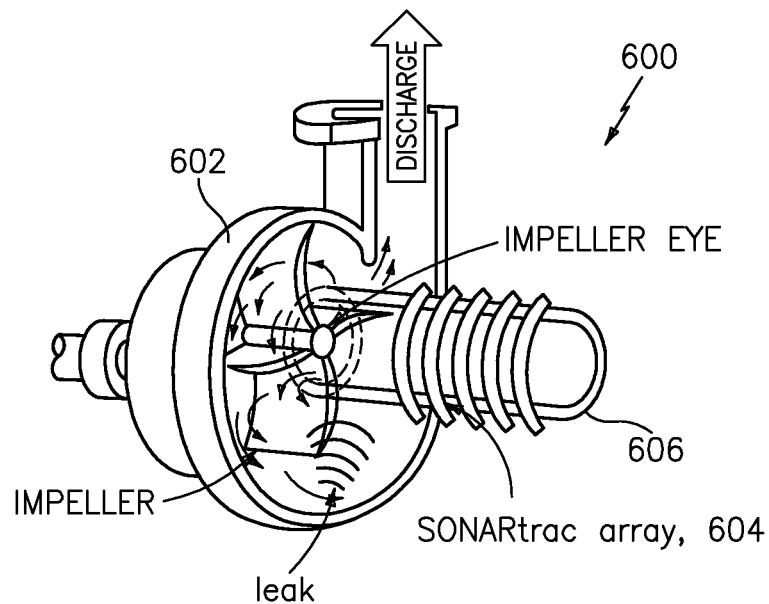
FIG. 6a is a block diagram of a pump system having pump leak detection based on acoustic emissions according to some embodiments of the present invention.
Figure 6B:
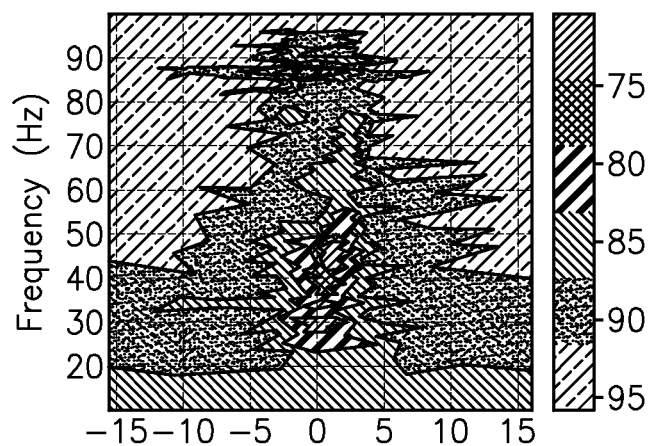

FIGS. 6a, 6b show a pump system generally indicated as 600 featuring a pump 602 and one or more SONAR-based arrays of sensors 604, along with the signal processing module, such as module 10 (FIGS. 1a, 1b), according to some embodiments of the present invention.

According to some embodiment of the present invention, the acoustic measurement abilities of the SONAR-based array 604 can be used to identify a specific high frequency. In addition, the array processing capabilities of the system, including the processor or signal processing module 10 (FIGS. 1a, 1b), can be used to check the coherence of the frequency signal and determine an emission direction.

As a person skilled in the art would appreciate, the many mating surfaces of the various components in pumps often lead to leaks. These leaks can go for extended periods of time before detection and lead to expensive repair and cleanup. Consistent with that described herein, the acoustic emissions of these leaks can be detected and monitored by SONAR-based processing and technology according to the present invention.

Additionally, by using the SONAR-based processing and technology according to the present invention, leaks can also be detected within the various components of the pump itself. Internal valves such as those used in bladder pumps and piston pumps can greatly reduce a pumps capacity and efficiency if they leak. The acoustic emissions from such a leak could be detected with this system.

For example, in FIG. 6a the pump may include, e.g., a bladder pump or a piston pump.

In FIG. 6a, the SONAR-based array 604 of sensors may be attached to one or more parts or surfaces of the pump 602, including an inlet 606 of the pump 602, and configured to respond to unsteady pressures caused by a medium flowing through the pump, including the leaks in the internal valves and around the bearings and mating surfaces leaks, and may be configured to provide a signal containing information about the same.

The signal processing module 10 (FIGS. 1a, 1b) may be configured to receive the signal containing information about the unsteady pressures caused by the medium flowing through the pump, and may also be configured to provide of an output signal containing information about pump leak detection, including information about the leaks in internal valves and around bearings and mating surfaces.

The pump system 600 or pump 602 may also include one or more elements, devices, apparatus or equipment that are known in the art, do not form part of the underlying invention, and are not disclosed herein or described in detail for that reason.

Pump Efficiency Monitor

According to some embodiment of the present invention, a technique is provided to monitor the performance of a pump using a SONAR-based flow meter to measure the flow rate of the pumped medium.

A SONAR-based flow meter, such as SONARtrac® VF-100 which is known in the art, can be used to measure the flow rate through the pump. The SONAR-based technique of flow rate measurement is especially beneficial for liquid slurry flows or particle-laden gas flows where, due to the erosive characteristics of the flow, any intrusive method of flow measurement would be subject to excessive wear and premature failure. The present invention of using a SONAR-based flow meter in combination with pressure and electrical power measurements enables pump efficiency to be monitored continuously and in real-time.

Some embodiments according to the present invention using this technique may take the form of a pump system featuring a pump; a SONAR-based array of sensors attached to one or more parts or surfaces of the pump, including an inlet of the pump, and configured to respond to unsteady pressures caused by a medium flowing through the pump, and to provide a signal containing information about the same; and a signal processing module that may be configured to receive the signal containing information about the unsteady pressures caused by the medium flowing through the pump, and may also be configured to provide of an output signal containing information about pump efficiency monitoring leak detection, based at least partly on the rate of flow of the medium through the pump.

According to some embodiment of the present invention, the signal processing module may be configured to provide the output signal based at least partly in response to signalling containing information about intake and discharge pressure and electrical power measurements.

Figure 7B:
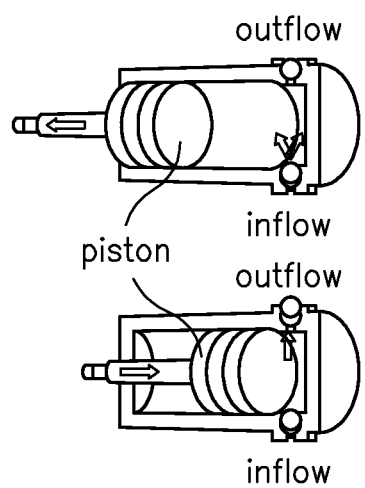
FIG. 7b is a diagram of a piston forming part of the positive displacement pump system shown in FIG. 7a being stroked inwardly and outwardly.

FIGS. 7a, 7b

Positive Displacement Pump Monitoring

FIGS. 7a, 7b show a pump system generally indicated as 700 featuring a positive displacement pump 702 and one or more SONAR-based arrays of sensors 704, along with the signal processing module, such as module 10 (FIGS. 1a, 1b), according to some embodiments of the present invention.

As a person skilled in the art would appreciate, positive displacements pumps operate by forcing fluid from an inlet pressure section of the pump into the discharge section. According to some embodiments of the present invention, the SONAR-based array may provide several mechanisms for monitoring the operation of these types of positive displacements pumps. Consistent with that described herein re centrifugal pumps, the performance of the pump can be monitored by measuring the flow produced by the pump 702 versus the number of pumping strokes. Both of these parameters can be measured by the SONAR-based flow meter. The meter in its normal mode of operation can give the material flow rate, while an analysis of the acoustic signals received can be used to track the pumping stroke rate.

Additional information on the wear rate of the pump can also be determined through a more detailed analysis of the acoustic emissions from the pump. The condition of a number of pump components, including seals, diaphragms and valves, can be ascertained from the acoustic signatures the components emit during operation. As an example, in a dual-valve piston style pump, each value may close depending on the stage of the pump. As each valve closes it will emit acoustic signals from the closure as well as possibly emit during the piston compression. The acoustic signature of the valve closing can determine if the valve is closing quickly and completely or if it is starting to wear, inducing more leakage and take additional time to close. Also, if the valve is not closing completely during the compression stage of the pump acoustic emissions of a leakage could be detected.

In addition, in diaphragm based positive displacement pump the critical diaphragm components could be monitored through its acoustic emissions. A hole or rip in the diaphragm could be detected as high frequency acoustics, while a periodic impulse may indicate a tear that is oscillating.

Some embodiments of the present invention using this technique may take the form of a pump system featuring such a positive displacement pump; a SONAR-based array of sensors attached to one or more parts or surfaces of the pump, and configured to respond to unsteady pressures and acoustic emissions caused by a medium flowing through the pump, and to provide a signal containing information about the same; and a signal processing module that may be configured to receive the signal containing information about the unsteady pressures and acoustic emissions caused by the medium flowing through the pump, and may also be configured to provide of an output signal containing information about positive displacement pump monitoring, based at least partly on the rate of flow of the pump versus the number of pumping strokes.

According to some embodiments of the present invention, the information about the rate of flow of the pump may be based at least partly on the unsteady pressures and the number of pumping strokes is based at least partly on the acoustic emissions.

The pump system 700 or pump 702 may also include one or more elements, devices, apparatus or equipment that are known in the art, do not form part of the underlying invention, and are not disclosed herein or described in detail for that reason.

Computer-Readable Storage Medium

According to some embodiments of the present invention, the apparatus may also take the form of a computer-readable storage medium having computer-executable components for performing the steps of the aforementioned method.

Applications Re Other Industrial Devices or Equipment

By way of example, the present invention is described in relation to, and part of, a pump system for pumping a medium through a pump. However, the scope of the invention is not intended to be limited to any particular type or kind of system or device for processing a flowing medium being monitored. For example, embodiments are envisioned using, and the scope of the invention is intended to include, other types or kinds of systems, or industrial devices or equipment either now known or later developed in the future.

THE SCOPE OF THE INVENTION

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
 a processor or signal processing module configured to
  receive an input signal containing information about sensed unsteady pressures or acoustic emissions caused by a medium flowing through a pump, the sensed unsteady pressures or acoustic emissions sensed by one or more Polyvinylidene Fluoride (PVDF) based or SONAR-based sensors arranged on, or integrated into, or externally attached or fixtured to, one or more parts of the pump, and
  provide an output signal containing information about wear of the one or more parts of the pump, based on the input signal received.

2. The apparatus according to claim 1, wherein the output signal contains information about a slip flow measurement that can be related to pump performance.

3. The apparatus according to claim 1, wherein the input signal contains information about the sensed unsteady pressures received from a SONAR-based array of sensors arranged in relation to a casing of the pump.

4. The apparatus according to claim 3, wherein the SONAR-based array is arranged in relation to a suction inlet, a discharge, or both.

5. The apparatus according to claim 3, wherein the SONAR-based array is integrated into the casing, or is externally fixtured to the pump.

6. The apparatus according to claim 1, wherein the sensed unsteady pressures are created by both the velocity of an impeller tip and the velocity of the medium.

7. The apparatus according to claim 1, wherein wear in either an impeller tip or a casing or liner of the pump, or both, causes a change in the sensed unsteady pressures.

8. The apparatus according to claim 1, wherein the processor or signal processing module is configured to determine the velocity of an impeller tip and the velocity of the medium in real time based at least partly on pressure measurements that are a function of the spacing between sensors in a SONAR-based array and the transition time between the sensors.

9. The apparatus according to claim 1, wherein the processor or signal processing module is configured to measure the slip of the pump and ideal velocities in an impeller of the pump based at least partly on the unsteady pressures.

10. The apparatus according to claim 1, wherein the processor or signal processing module is configured to determine a convection velocity based at least partly on the unsteady pressures.

11. The apparatus according to claim 1, wherein the processor or signal processing module is configured to determine the velocity of the medium flowing in a discharge and suction end of the pump based at least partly on the unsteady pressures.

12. The apparatus according to claim 1, wherein the output signal contains information about high velocities present within an impeller of the pump that can cause accelerated wear on a back shroud of the impeller based at least partly on the sensed unsteady pressures.

13. The apparatus according to claim 1, wherein the apparatus comprises the one or more SONAR-based sensors configured to sense and respond to the unsteady pressures caused by the medium flowing through the pump, and to provide SONAR-based sensed signaling containing information about the sensed unsteady pressures caused by the medium flowing through the pump.

14. The apparatus according to claim 1, wherein the input signal contains information about the sensed acoustic emissions caused by the medium flowing through the pump, and the processor or signal processing module is configured to monitor the sensed acoustic emissions traveling in the medium flowing in the pump, including in the medium flowing on either an inlet or an outlet of the pump.

15. The apparatus according to claim 1, wherein the processor or signal processing module is configured to detect pump leak conditions, including leaks around bearings, mating surfaces, internal valves including those used in a bladder pump or a piston pump, based at least partly on the sensed acoustic emissions.

16. The apparatus according to claim 1, wherein the processor or signal processing module is configured to monitor pump efficiency, based at least partly on measuring a rate of flow of the medium through the pump, pressures at an intake and a discharge of the pump, and power provided to an electric motor driving the pump.

17. The apparatus according to claim 16, wherein the processor or signal processing module is configured to monitor the pump efficiency continuously and in real time.

18. The apparatus according to claim 1, wherein the apparatus comprises a pump system having:
a pump; and
the one or more SONAR-based sensors, arranged on, or integrated into, or externally attached or fixtured to the one or more parts of the pump, configured to respond to unsteady pressures caused by the medium flowing through the pump, and to provide associated signaling containing information about the sensed unsteady pressures caused by the medium flowing through the pump.

19. The apparatus according to claim 1, wherein the apparatus comprises a pump system having:
a pump having a casing or a liner;
a SONAR-based array of sensors arranged on the casing or liner, and configured to respond to unsteady pressures caused by a medium flowing through the pump, including the unsteady pressures caused by an impeller tip velocity and a fluid velocity, and to provide a signal containing information about the unsteady pressures caused by the impeller tip velocity and the fluid velocity; and
the signal processor or processing module configured to receive the signal containing information about the unsteady pressures caused by the impeller tip velocity and the fluid velocity, and also configured to provide the output signal containing information about a slip flow measurement related to wear of the pump.

20. The apparatus according to claim 19, wherein the signal processor or processing module is configured to determine the impeller tip velocity and the fluid velocity of the medium in real time based at least partly on pressure measurements that are a function of the spacing between sensors in the SONAR-based array and the transition time between the sensors.

21. The apparatus according to claim 1, wherein the apparatus comprises a pump system having:
a pump having an impeller, a casing, a suction inlet or a discharge;
a SONAR-based array of sensors arranged on the casing, suction inlet or discharge, and configured to respond to unsteady pressures caused by a medium flowing through the pump, and to provide a signal containing information about the unsteady pressures caused by the medium flowing through the pump; and
the signal processor or processing module configured to receive the signal, and also configured to provide the output signal containing information about wear of the one or more parts of the pump, including wear in the back shroud or eye of the impeller.

22. The apparatus according to claim 1, wherein the apparatus comprises a pump system comprising:
a pump, including a bladder pump or a piston pump;
a SONAR-based array of sensors attached to the one or more parts or surfaces of the pump, including an inlet of the pump, and configured to sense and respond to unsteady pressures caused by a medium flowing through the pump, including leaks in internal valves and around bearings and mating surfaces leaks, and to provide a signal containing information about the unsteady pressures caused by the medium flowing through the pump, including the leaks in the internal valves and around the bearings and mating surfaces leaks; and
the signal processor or processing module configured to receive the signal, and also configured to provide the output signal containing information about pump leak detection, including information about wear associated with leaks in internal valves and around bearings and mating surfaces.

23. The apparatus according to claim 22, wherein the signal processor or processing module is configured to check the coherence of a frequency signal and determine an emission direction that can be used for the pump leak detection.

24. The apparatus according to claim 1, wherein the apparatus comprises a pump system having:
a pump;
a SONAR-based array of sensors attached to the one or more parts or surfaces of the pump, including an inlet of the pump, and configured to sense and respond to unsteady pressures caused by a medium flowing through the pump, and to provide a signal containing information about the unsteady pressures caused by the medium flowing through the pump; and
the signal processor or signal processing module configured to receive the signal, and also configured to provide the output signal containing information about wear associated with pump efficiency monitoring leak detection, based at least partly on the rate of flow of the medium through the pump.

25. The apparatus according to claim 24, wherein the signal processor or processing module is configured to provide the output signal based at least partly in response to signalling containing information about intake and discharge pressure and electrical power measurements.

26. The apparatus according to claim 1, wherein the apparatus further comprises: the one or more Polyvinylidene Fluoride (PVDF) based sensors, or the SONAR-based sensors, or the combination thereof.

27. Apparatus comprising:
a processor or signal processing module configured to
receive an input signal containing information about sensed unsteady pressures and/or acoustic emissions caused by a medium flowing through a pump, and
provide an output signal containing information about the performance of the pump,
wherein the output signal contains information about low velocities present within an impeller of the pump that can cause accelerated wear on an eye of the impeller, including excessive wear due to recirculation of slurry back to the eye, based at least partly on the sensed unsteady pressures.

28. Apparatus comprising:
a processor or signal processing module configured to
receive an input signal containing information about sensed unsteady pressures and sensed acoustic emissions caused by a medium flowing through a pump,
determine when cavitation occurs in the pump based at least partly on the sensed acoustic emissions, and
provide an output signal containing information about wear of one or more parts of the pump, based on the input signal received,
wherein the input signal contains information about the sensed acoustic emissions received from one or more Polyvinylidene Fluoride (PVDF) based sensors arranged in relation to the one or more parts of the pump.

29. The signal processing module according to claim 28, wherein the Polyvinylidene Fluoride (PVDF) based sensors are located in multiple locations, including on the body of the pump itself, or along piping attached to the pump.

30. The signal processing module according to claim 28, wherein the Polyvinylidene Fluoride (PVDF) based sensors are attached to an inlet side of the pump, including a centrifugal pump.

31. Apparatus comprising:
a processor or signal processing module configured to
receive an input signal containing information about sensed unsteady pressures caused by a medium flowing through a pump, and
provide an output signal containing information about wear of one or more parts of the pump, based on the input signal received,
wherein the input signal contains information about the acoustic emissions received from one or more Polyvinylidene Fluoride (PVDF) based sensors arranged in relation to the pump.

32. The apparatus according to claim 31, wherein the one or more Polyvinylidene Fluoride (PVDF) based sensors are attached to the inside or the outside of piping arranged in relation to the pump.

33. The apparatus according to claim 31, wherein the processor or signal processing module is configured to detect conditions, including cavitation, bearing wear, impeller wear and casing lining damage, based at least partly on the sensed acoustic emissions.

34. The apparatus according to claim 31, wherein the processor or signal processing module is configured to determine a pump signature of the sensed acoustic emissions during normal steady-state operation of the pump taken with the one or more Polyvinylidene Fluoride (PVDF) based sensors.

35. The apparatus according to claim 34, wherein the processor or signal processing module is configured to determine variations in frequency or amplitude in relation to the pump signature that can indicate pump wear and potential failure.

36. The apparatus according to claim 31, wherein the processor or signal processing module is configured to measure and identify one or more specific high frequencies related to pump leak conditions, based at least partly on the sensed acoustic emissions.

37. The apparatus according to claim 31, wherein the processor or signal processing module is configured to check the coherence of a frequency signal and determine an emission direction.

38. The apparatus according to claim 31, wherein the processor or signal processing module is configured to measure a rate of flow of the medium through a positive displacement pump versus the number of pumping strokes of the positive displacement pump.

39. The apparatus according to claim 38, wherein the measurement of the rate of flow of the medium is based at least partly on the sensed unsteady pressures and the measurement of the number of pumping strokes of the positive displacement pump is based at least partly on the sensed acoustic emissions.

40. The apparatus according to claim 38, wherein the processor or signal processing module is configured to monitor the condition of one or more pump components, including seals, diaphragms, valves, based at least partly on the sensed acoustic emissions.

41. The apparatus according to claim 38, wherein the processor or signal processing module is configured to monitor the condition of a dual valve piston style pump, including closing of valves and piston compression, based at least partly on the sensed acoustic emissions.

42. A signal processing module comprising:
one or more modules configured to receive an input signal containing information about sensed unsteady pressures and/or acoustic emissions caused by a medium flowing through a pump, and also configured to provide an output signal containing information about the performance of the pump;
the one or more modules configured to measure a rate of flow of the medium through a positive displacement pump versus the number of pumping strokes of the positive displacement pump;
the one or more modules configured to monitor the condition of a dual valve piston style pump, including closing of valves and piston compression, based at least partly on the sensed acoustic emissions;
wherein the one or more modules configured to monitor the condition of the closing of valves to detect if a valve is closing to quickly and completely, or if the valve is starting to wear, including providing more leakage or taking additional time to close, or if the valve is not closing completely during the compression stage where pump acoustic emissions of a leakage can be detected.

43. A signal processing module comprising:
one or more modules configured to receive an input signal containing information about sensed unsteady pressures and/or acoustic emissions caused by a medium flowing through a pump, and also configured to provide an output signal containing information about wear of one or more parts of the pump;

wherein the one or more modules configured to measure a rate of flow of the medium through a positive displacement pump versus the number of pumping strokes of the positive displacement pump; and wherein the one or more modules configured to monitor the condition of a diaphragm-based positive displacement pump, based at least partly on the sensed acoustic emissions, including monitoring for a hole or a rip in a diaphragm that could be detected as high frequency acoustics, or monitoring for a tear that is oscillating in the diaphragm that could be detected as a periodic pulse.

44. A pump system comprising:

a positive displacement pump;

a SONAR-based array of sensors and one or more Polyvinylidene Fluoride (PVDF) based sensors attached to parts or surfaces of the pump, and configured to respond to unsteady pressures and acoustic emissions caused by a medium flowing through the pump, and to provide a signal containing information about the unsteady pressures and acoustic emissions caused by the medium flowing through the pump; and a signal processing module configured to receive the signal containing information about the unsteady pressures and acoustic emissions caused by the medium flowing through the pump, and also configured to provide an output signal containing information about positive displacement pump monitoring, based at least partly on the rate of flow of the pump versus the number of pumping strokes.

45. The pump system according to claim 44, wherein the information about the rate of flow of the pump is based at least partly on the unsteady pressures, and the number of pumping strokes is based at least partly on the acoustic emissions.

* * * * *